United States Patent
Splinter et al.

(10) Patent No.: US 9,000,168 B2
(45) Date of Patent: Apr. 7, 2015

(54) METHODS FOR OBTAINING CYCLOPAMINE

(75) Inventors: Steven Splinter, North Vancouver (CA); Satyasagar Kadali, Burlington (CA)

(73) Assignee: Radient Technologies Inc., Edmonton, Alberta (CA)

( * ) Notice: Subject to any disclaimer, the term of this patent is extended or adjusted under 35 U.S.C. 154(b) by 690 days.

(21) Appl. No.: 12/737,297

(22) PCT Filed: Jul. 3, 2009

(86) PCT No.: PCT/CA2009/000916
§ 371 (c)(1), (2), (4) Date: Jan. 18, 2011

(87) PCT Pub. No.: WO2010/000070
PCT Pub. Date: Jan. 7, 2010

(65) Prior Publication Data
US 2011/0160457 A1 Jun. 30, 2011

(30) Foreign Application Priority Data
Jul. 4, 2008 (CA) .................................. 2636807

(51) Int. Cl.
| | |
|---|---|
| C07D 211/00 | (2006.01) |
| C07D 401/00 | (2006.01) |
| C07D 311/96 | (2006.01) |
| C07D 307/94 | (2006.01) |
| C07J 21/00 | (2006.01) |
| C07J 43/00 | (2006.01) |
| C07J 69/00 | (2006.01) |

(52) U.S. Cl.
CPC ............... *C07J 21/00* (2013.01); *C07D 307/94* (2013.01); *C07D 311/96* (2013.01); *C07J 43/00* (2013.01); *C07J 69/00* (2013.01)

(58) Field of Classification Search
CPC .. C07D 491/10; C07D 471/10; C07D 311/96; C07D 307/94
USPC ............................... 546/18, 15; 549/331, 345
See application file for complete search history.

(56) References Cited

U.S. PATENT DOCUMENTS
2010/0003728 A1    1/2010  Jayatilake et al.

OTHER PUBLICATIONS

Handa et al, Extraction Technologies for Medicinal and Aromatic Plants (2008).*

(Continued)

*Primary Examiner* — Andrew D Kosar
*Assistant Examiner* — Raymond Covington
(74) *Attorney, Agent, or Firm* — Collard & Roe, P.C.

(57) ABSTRACT

The present invention relates to a process for extracting, purifying and isolating cyclopamine from cyclopamine-containing biomass comprising the steps of contacting cyclopamine-containing organic matter with an extractant (e.g., aqueous extractant) capable of extracting cyclopamine, separating the extracted organic matter from the cyclopamine/extract solution, concentrating the cyclopamine/extract solution leaving a concentrated aqueous solution, contacting the concentrated aqueous solution with an organic extractant capable of selectively extracting cyclopamine from the aqueous phase, concentrating the cyclopamine-containing organic phase, providing an enriched extract containing cyclopamine, separating cyclopamine from the enriched extract using column chromatography, providing at least one fraction containing cyclopamine, and crystallizing select chromatography fractions to provide purified cyclopamine.

20 Claims, 2 Drawing Sheets

(56) References Cited

OTHER PUBLICATIONS

Bart, Industrail Scale Natural Products Extraction, pp. 1-25 (2011).*
Kaufmann et al Phytochem. Anal. vol. 13 pp. 105-113 (2002).*
International Search Report.
Cooper, et al., "Teratogen-Mediated Inhibition of Target Tissue Response to Shh Signaling", *Science* 280, 1998; pp. 1603-1607.
Incardona, et al., "The teratogenic Veratrum alkaloid cyclopamine inhibits Sonic hedgehog signal transduction", *Development 125*, 1998; pp. 3553-3562.
Katano, "Hedgehog signaling pathway as therapeutic target in breast cancer", *Cancer Letters*, 2005; 227, pp. 99-104.
Chen, et al., Hedgehog signal pathway is activated in ovarian carcinomas, correlating with cell proliferation: It's inhibition leads to growth suppression and apoptosis, *Cancer Sci.*, 2007; vol. 98, No. 1, pp. 68-76.
Keeler, et al., "Teratogenic Compounds of *Veratrum californicum* (Durand): I. Preparation and Characterization of Fractions and Alkaloids for Biologic Testing", *Canadian Journal of Biochemistry*, 1966; vol. 44, pp. 819-828.
Oatis Jr., et al., "Isolation, purification, and full NMR assignments of cyclopamine from *Veratrum californicum*", *Chemistry Central Journal*, 2008; 2:12, pp. 1-6.
Qualtrough, et al., "Hedgehog Signalling in Colorectal Tumour Cells: Induction of Apoptosis With Cyclopamine Treatment", *Int. J. Cancer*, 2004; 110, pp. 831-837.
Sanchez, et al., "In vivo inhibition of endogenous brain tumors through systemic interferences of Hedgehog signaling in mice", *Mechanism of Development*, 2005; 122, pp. 223-230.
Thayer, et al., "Hedgehog is an early and late mediator of pancreatic cncer tumorigenesis", *Nature*, 2003, vol. 425, pp. 851-856.
Taş, et al., "Rapid Clearance of Psoriatic Skin Lesions Induced by Topical Cyclopamine", *Dermatology*, 2004; 209, pp. 126-131.
Keeler, "Cyclopamine and Related Steroidal Alkaloid Teratogens: Their Occurrence, Structural Relationship, and Biologic Effects", *LIPIDS*, 1978; vol. 13, No. 10, pp. 708-715.
Keeler, "Teratogenic Compounds of *Veratrum californicum* (Durand)—IV. First Isolation of Veratramine and Alkaloid Q and a Reliable Method for Isolation of Cyclopamine", *Phytochemistry*, 1968; vol. 7, pp. 303-306.
Keeler, "Teratogenic Compounds of *Veratrum californicum* (Durand)—VI. The Structure of Cyclopamine", *Phytochemistry*; 1969; vol. 8, pp. 223-225.
Keeler, et al., "Teratogenic Compounds of *Veratrum californicum* as a Function of Plant Part, Stage, and site of Growth", *Phytochemistry*, 1971; vol. 10, pp. 1765-1769.
Masamune, et al., "A New Alkaloid from *Veratrum* Species", *Tetrahedron Letters*, 1964; No. 16, pp. 913-917.
Mimeault, et al., "Cytotoxic effects induced by a combination and gefitinib, the selective hedgehog and epidermal growth factor receptor signaling inhibitors in prostate cancer cells", *Int. J. Cancer*, 2006; 118, pp. 1022-1031.

\* cited by examiner

METHODS FOR OBTAINING CYCLOPAMINE

CROSS REFERENCE TO RELATED APPLICATIONS

This application is the National Stage of PCT/CA2009/000916 filed on Jul. 3, 2009, which claims priority under 35 U.S.C. §119 of Canadian Application No. 2,636,807 filed on Jul. 4, 2008, the disclosure of which is incorporated by reference. The international application under PCT article 21(2) was published in English.

FIELD OF THE INVENTION

This invention relates to methods for the extraction, purification and isolation of cyclopamine from organic matter containing cyclopamine, including but not limited to *Veratrum* plants.

BACKGROUND OF THE INVENTION

Figure 1:
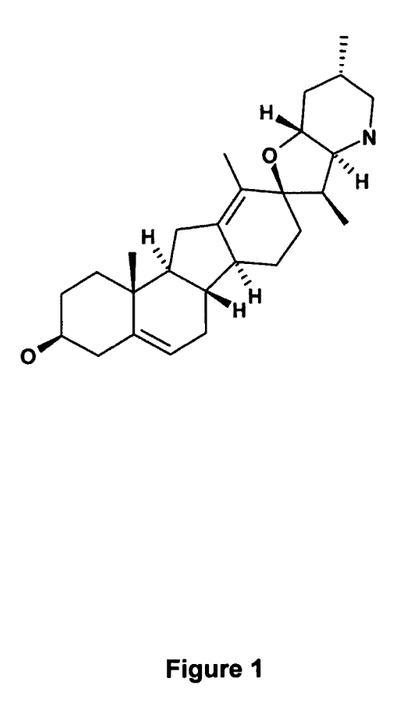
FIG. 1 shows the formula for cyclopamine.
Figure 2:
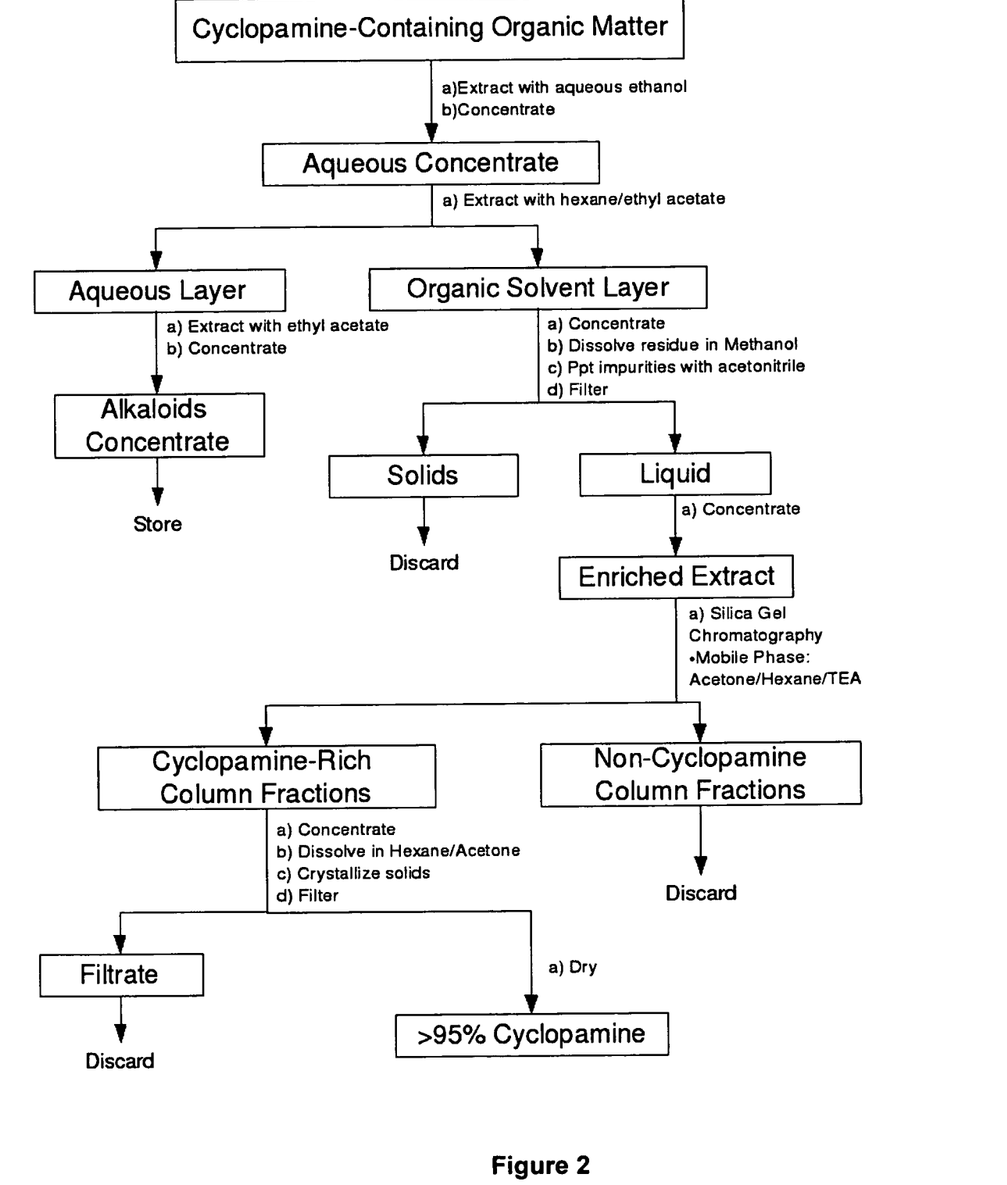
FIG. 2 is a flow diagram outlining a preferred embodiment of the methods of the present invention.

Cyclopamine (11-deoxojervine) is a steroidal alkaloid that occurs naturally in plants of the genera *Veratrum, Zigadenus, Schoenocaulon*[1] and others. Its formula is $C_{27}H_{41}NO_2$ with a molecular weight of 411.63. The structure of cyclopamine is shown in FIG. 1.

1 R. F. Keeler, Lipids 13 (1978) pp. 708-715.

FIG. 1

An epidemic of sheep congenital deformities during the 1950's was eventually traced to the presence of the alkaloids jervine and cyclopamine in the wild lily *Veratrum californicum* upon which the sheep grazed[2,3]. It is now known that these teratogenic effects of jervine and cyclopamine are due to their specific inhibition of cellular responses to the Hedgehog (Hh) family of secreted growth factors[4,5]. In accordance with this general mechanism of hedgehog pathway activity, cyclopamine and related compounds have shown promise in the treatment of diverse cancers. These include for example brain tumors[6], breast cancer[7], ovarian cancer[8], prostate cancer[9], colorectal cancer[10] and pancreatic cancer11. Although the primary focus has been on cancer, cyclopamine and its analogues are also being explored in a large number of other clinical conditions where a therapeutic effect can be obtained for a condition or disorder by inhibiting one or more aspects of Hedgehog pathway activity, including for example psoriasis[12].

2 R. F. Keeler, Phytochemistry 7 (1968) pp. 303-306.
3 R. F. Keeler and W. Binns, Phytochemistry 10 (1971) pp. 1765-1769.
4 M. K. Cooper, J. A. Porter, K. E. Young and P. A. Beachy, Science 280 (1998) pp. 1603-1607.
5 J. P. Incardona, W. Gaffield, R. P. Kapur and H. Roelink, Development 125 (1998) pp. 3553-3562.
6 P. Sanchez, A. Ruiz i Altaba, Mech. Dev. 22 (2005) pp. 223-230.
7 M. Katano, Cancer Lett. 227 (2005) pp. 99-104.
8 X. Chen, A. Horiuchi, N. Kikuchi, R. Osada, J. Yoshida, T. Shiozawa, K. Konishi, Cancer Sci. 98 (2007) pp. 68-76.
9 M. Mimeault, E. Moore, N. Moniaux, J. P. Henichart, P. Depreux, M. F. Lin, S. K. Batra, Int. J. Cancer 118 (2006) pp. 1022-1031.
10 D. Qualtrough, A. Buda, W. Gaffield, A. C. Williams, C. Paraskeva, Int. J. Cancer 110 (2004) pp. 831-837.
11 S. P. Thayer, M. Pasca di Magliano, P. W. Heiser, C. M. Nielsen, D. J. Roberts, G. Y. Lauwers, Y. P. Qi, S. Gysin, C. Fernandez-del Castillo, V. Yajnik, B. Antoniu, M. McMahon, A. L. Warshaw, M. Hebrok, Nature 425 (2003) pp. 851-856.
12 S. Tas and O. Avci, Dermatology 209 (2004) pp. 126-131.

Cyclopamine was first isolated from *V. grandiflorum* in 1964[13] and later from *V. californicum*[2,3]. Cyclopamine was isolated in small amounts by extraction of alkanized ground plant roots with benzene, and subsequent purification by recrystallization in acetone/water and then methanol/water followed by silica gel column chromatography using a benzene/methanol mobile phase. This method results in very low recovery of the available alkaloids and cannot be easily scaled up. Recently, Oatis et al.[14] published a method for isolating cyclopamine from *V. californicum* by extracting kilogram-sized batches of biomass in a Soxhlet extractor using refluxing benzene for 14 hours. The benzene solution was then passed through a silica gel column and the trapped cyclopamine eluted using stepped gradient dicholormethane-isopropanol solutions. Cyclopamine-rich fractions were then re-chromatographed with ethyl acetate as the mobile phase and the resulting fractions triturated with acetone and recrystallized from ethanol-water to give purified cyclopamine. The final recovery was reported at approximately 55% of the available cyclopamine. This process is not scalable to large volumes. Benzene is a known carcinogen and dicholormethane, and other chlorinated hydrocarbons, are recognized as toxic and potentially carcinogenic and so it is desirable to avoid utilizing either in large scale processes. No other published methods for purifying cyclopamine from natural sources exist.

13 T. Masamune, T. Mori, M. Takasugi and A. Mural, *Tetrahedron Lett.* 16 (1964) pp. 913-917.
14 J. E. Oatis, P. Brunsfeld, J. W. Rushing, P. D. Moeller, D. W. Bearden, T. N Gallien and G. Cooper, Chemistry Central Journal 2 (2008) p. 12.

The molecular complexity of cyclopamine suggests that a total synthesis from readily available raw material is not likely to be economically feasible. Preparation of pharmaceuticals and pharmaceutical compositions based on cyclopamine and its analogues and derivatives will therefore depend on a supply of the purified compound from natural sources. It is therefore of great interest to develop efficient methods of extracting, purifying and isolating cyclopamine from organic matter. No prior art exists for efficient, industrial-scale extraction, purification and isolation of cyclopamine. This invention provides such a method.

SUMMARY OF THE INVENTION

An object of the present invention is to provide methods for obtaining high purity cyclopamine from cyclopamine-containing organic matter. More specifically, the invention provides methods to extract, purify and isolate cyclopamine from natural sources, in particular plants and more specifically *Veratrum californicum*. These methods have the advantage of being simple and cost effective and yielding cyclopamine in high yield on an industrial scale. Furthermore, these methods have the advantage of ensuring the stability of cyclopamine for use as an active pharmaceutical ingredient or as a raw material in the preparation of cyclopamine-related derivatives and analogues for use in clinical conditions where a therapeutic effect can be obtained for a condition or disorder by inhibiting one or more aspects of Hedgehog pathway activity. Still further, this invention provides methods to separate other valuable steroidal alkaloids, including but not limited to jervine, veratramine and cyclopasine, present in certain cyclopamine-containing organic matter.

One aspect of this invention provides a process for extracting, purifying and isolating cyclopamine from cyclopamine-containing biomass comprising the steps of:
(a) Contacting cyclopamine-containing organic matter with an aqueous extractant (e.g., water-containing extractant) capable of extracting cyclopamine;
(b) Separating the extracted organic matter from the cyclopamine/extract solution;
(c) Concentrating the cyclopamine/extract solution leaving a concentrated aqueous solution;
(d) Contacting the concentrated aqueous solution with an organic extractant capable of selectively extracting cyclopamine from the aqueous phase;
(e) Concentrating the cyclopamine-containing organic phase, providing an enriched extract containing cyclopamine;
(f) Separating cyclopamine from the enriched extract using column chromatography, providing at least one fraction containing cyclopamine; and
(g) Crystallizing select chromatography fractions to provide purified cyclopamine.

Another aspect of the invention relates to an improvement to the process, the improvement being the preparation of a second residue following the initial extraction of cyclopamine-containing organic matter, that is more highly concentrated in cyclopamine and so reduces the complexity and cost of subsequent finishing treatments designed to further purify or isolate the cyclopamine, and wherein the improvement comprises the steps of:
(a) contacting cyclopamine-containing organic matter with an extractant (e.g., aqueous extractant) capable of extracting and stabilizing cyclopamine;
(b) separating the extracted organic matter from the cyclopamine/extract solution;
(c) concentrating the cyclopamine/extract solution to form a first residue;
(d) partitioning the residue between an aqueous phase and an organic solvent or solvent mixture capable of dissolving the cyclopamine to produce an aqueous phase and an organic phase;
(e) separating the organic phase from the aqueous phase and recovering the organic phase substantially free of the aqueous phase;
(f) forming a second residue from the organic phase enriched in cyclopamine.

In a preferred aspect of the invention, the second residue may then optionally be subjected to a finishing treatment to further purify or isolate cyclopamine, including but not limited to liquid-liquid extraction, precipitation, crystallization, chromatography or mixtures thereof.

In another aspect of the invention, the aqueous phase from step (e) can be recovered substantially free of the organic phase and subjected to a further finishing treatment to recover other steroidal alkaloids, including but not limited to jervine, veratramine and cyclopasine, present in certain cyclopamine-containing organic matter, such finishing treatment including but not limited to liquid-liquid extraction, precipitation, crystallization, chromatography or mixtures thereof.

Another aspect of this invention relates to an improvement to the process wherein the improvement comprises the steps of contacting cyclopamine-containing biomass with an aqueous alcohol solution (e.g. water-containing alcohol solution) that is made basic or alkaline and so extracts and stabilizes the cyclopamine, separating the extracted biomass from the cyclopamine/extract solution and concentrating the cyclopamine/extract solution to form a residue concentrated in cyclopamine, the improvement being the elimination of the need to employ a toxic extractant in the first step, and the reduction or elimination of the decomposition of cyclopamine.

In a preferred aspect of the invention the cyclopamine-containing organic matter is first extracted using microwave-assisted extraction.

In a particularly preferred embodiment, cyclopamine is extracted from cyclopamine-containing biomass in a multi-step process by carrying out Steps 1-4 or Steps 1-5, then purified and isolated by carrying out Steps 1-4 followed by Steps 6 and 7 or alternatively by carrying out Steps 1-7:

Step 1. Biomass Extraction

Dried, milled *V. californicum* biomass is extracted using ethanol/water (v/v) as the extraction solvent. The biomass or solvent is first mixed with a small amount of sodium carbonate to ensure that basic conditions are maintained during extraction in order to protect against decomposition of the cyclopamine molecule. The extracted solids (marc) are separated from the solvent/product mixture (micella). Residual solvent that is held up in the marc is recovered by steam injection in a desolventizer and the spent biomass solids are collected for disposal. The micella is collected for further processing.

Optimized extraction parameters are as follows:
Biomass Input: Dried, milled *V. californicum*.
Extraction Solvent: 67% Ethanol/33% water (v/v) Ethanol:
Sodium Carbonate: 0.015 kg/L solvent
Liquid-to-Solid Ratio: 4.5 L/kg
Microwave Extraction Time: 5 minutes
Post-Microwave Mix Time: 25 minutes
Total Extraction Time: 30 minutes Step 2: Micella Concentration The micella from the extraction step is concentrated in a vacuum evaporator. The evaporated azeotropic ethanol/water mixture is condensed and collected for re-use. The micella is concentrated to approximately 20 to 25% of its original volume, leaving a basic aqueous layer that is collected for purification of cyclopamine by liquid-liquid (L/L) extraction. Optimized evaporation conditions are as follows:
Temperature: 45 to 50° C.
Vacuum: 25 mm Hg Step 3: Liquid-Liquid Extraction The concentrated aqueous solution from Step 2 is extracted with a mixture of hexanes and ethyl acetate to recover and purify cyclopamine. The cyclopamine is recovered into the organic layer which is concentrated to produce an "enriched" extract for further processing. Three extractions are carried out to optimize the cyclopamine recovery. The depleted aqueous layer is then either sent for disposal or extracted again using ethyl acetate to recover residual, non-cyclopamine alkaloids. Optimized liquid-liquid extraction conditions are as follows:
Organic Solvent: 70% hexanes/30% Ethyl Acetate (v/v)
Organic/Aqueous Ratio: 1:1 (v/v)
Mixing Time: 15 minutes
Settling Time: 60 minutes Step 4: Concentration of Organic Layer The organic layer from Step 3 is concentrated to dryness in a vacuum evaporator to give an extract "enriched" to approximately 12 to 13% cyclopamine. The evaporated hexanes/ ethyl acetate are recovered for re-use. Optimized evaporation conditions are as follows:

Temperature: 35 to 40° C.
Vacuum: 25 mm Hg

Step 5 Optional Pre-Column Precipitation of Polar Compounds

An optional step can be used for cases where the enriched extract is of lower cyclopamine purity. In these cases, a less concentrated enriched extract results in very inefficient column chromatography and reduced cyclopamine yields. To increase the purity of the enriched extract, the extract is first dissolved in methanol and acetonitrile is added to precipitate resins and other high polarity compounds. The precipitate is removed by filtration and discarded and the filtrate concentrated. Optimized precipitation conditions are as follows:

Dissolution Solvent: methanol
Dissolution Temperature/Time: 70° C./20 minutes
Precipitation Solvent: acetonitrile (5 L/L methanol)
Mixing Temperature/Time: 50° C./10 minutes
Precipitation Temperature/Time: 4° C./8 hours Step 6: Column Chromatography The cyclopamine is further purified by normal phase column chromatography using silica gel as the stationary phase and an isocratic mobile phase mixture of acetone/toluene/triethylamine. The enriched extract from step 4 is first adsorbed onto silica gel and then loaded on a conditioned column and eluted under medium pressure. Fractions are combined and analyzed against a cyclopamine standard using thin layer chromatography (TLC). Appropriate fractions are then combined, concentrated and stored for final isolation of cyclopamine by crystallization.

Optimized column chromatography conditions are as follows:

Stationary Phase: Silica Gel (230-400 mesh)
Mobile Phase Acetone:Toluene:TEA 47.75:47.75:0.5 (v/v/v)
Column Loading: 0.12 to 0.15 kg extract/kg silica gel
Column Pressure: 30 psig
Mobile Phase Flowrate: 12 L/h Step 7: Cyclopamine Crystallization Purified cyclopamine is obtained by dissolving the dried fractions from column chromatography in a mixture of hexanes/acetone and crystallizing cyclopamine by chilling. The final product is dried and analysed for cyclopamine by HPLC, LC/MS and NMR. The final product is >95% pure cyclopamine. Optimized crystallization conditions are as follows:

Crystallization Solvent: 70% Hexanes/30% Acetone (v:v)
Solvent/Extract Ratio: 2 L/kg
Dissolution Temperature: 50 to 60° C.
Crystallization Temperature: 2 to 8° C.
Crystallization Time: 6 hours

DETAILED DESCRIPTION OF THE INVENTION

The features and other details of the invention will now be particularly described.

The methods of the invention begin with contacting cyclopamine-containing organic matter with an extractant capable of extracting cyclopamine. Organic matter is herein meant to include any matter containing or derived from living organisms. In a preferred aspect of the invention, the organic matter is plant matter of the genera *Veratrum, Zigadenus*, or *Schoenocaulon*. In a more preferred aspect, the organic matter is *Veratrum californicum* biomass. Extractants capable of extracting cyclopamine include for example alkanes, alcohols, aromatics, ketones, esters, halogenated hydrocarbons and mixtures and aqueous mixtures thereof. In a preferred aspect, the extraction of organic matter containing cyclopamine is achieved using a lower alcohol, including but not limited to, methanol, ethanol, or aqueous methanol or aqueous ethanol or combinations thereof providing a first crude alcoholic extract.

While the plant matter to be extracted may be used in fresh form, it is preferably dried prior to extraction in order to increase its shelf-life and minimize decomposition. Preferably, the plant material is dried to a residual moisture content of less than about 20% by weight. More preferably, the plant material is dried to a residual moisture content of less than about 10% by weight.

While the plant matter to be extracted may be used in substantially intact form, it is preferably manipulated to increase the surface area and so improve the extraction efficiency. Methods to manipulate the plant matter to increase the surface area will be known to those skilled in the art. Preferably, the plant matter is cut, chopped, crushed, or milled or manipulated by mechanical means to form a powder. Preferably the plant matter is ground to a particle size of between about 8 to 10 mesh.

The contacting of organic matter with extractant in this or any embodiment may be by any suitable means as are known in the art; including but not limited to, percolation, immersion, agitation, soxhlet extraction, countercurrent extraction, and ultrasound-assisted extraction. Extraction is usually conducted for prolonged periods of at least four hours, and typically between 8 and 24 hours. The extractant is preferably added in an amount of about 4 to 20 liters per kg of organic matter. Multiple extractions of the plant matter may be employed to enhance extraction.

Following extraction, the extracted organic matter is separated from the cyclopamine/extract solution by any suitable means as are known in the art, including but not limited to centrifugation, filtration, gravity separation or settling/decanting. To improve extraction efficiency, the extracted organic matter may be washed with fresh or lean extractant one or more times to remove all or most of the cyclopamine-containing extract that is held up within the extracted organic matter following separation. The remaining extractant that is held up in the extracted organic matter may then be removed, recovered and recycled by any means known in the art, including but not limited to direct or indirect steam desolventization.

The cyclopamine-containing extract solution is then concentrated to form a first residue. It will become clear to those skilled in the art that this concentration can be effected by any suitable means, including preferably vacuum evaporation. The residue may be a solid or a concentrated liquid. In a preferred embodiment, the concentration is effected under reduced pressure and at a temperature below which the thermal decomposition of cyclopamine is minimized. Preferably, the concentration is effected at a pressure less than about 25 mm Hg and a temperature less than about 50° C. More preferably, the concentration is effected at a temperature less than 45° C.

In one aspect of the invention, the first residue is partitioned between an aqueous phase and an organic phase such that the cyclopamine is preferentially taken up in the organic phase while various impurities present in the first residue are removed in the aqueous phase. This separation, also known as liquid-liquid partitioning, liquid-liquid separation, or liquid-liquid extraction, is based on the transfer of component(s) from one liquid phase into another immiscible liquid phase. Liquid-liquid separation relies on the different relative solubilities of component(s) in the two immiscible liquids. In particular, the component(s) is allowed to mix freely with two immiscible liquids, until it partitions between the two liquid phases thus formed such that the component(s) will generally be dissolved in one of the liquid phases to a greater extent than in the other liquid phase. Separation is then facilitated by the formation of two separate liquid layers, also known as phases. It will become clear to those skilled in the art, that the liquid-liquid partitioning can be achieved by any known means, including but not limited to tank mixing/settling, or counter-current liquid-liquid extraction schemes. Multiple extractions can be performed to improve the recovery of cyclopamine.

Aqueous and organic solvents and solvent mixtures which are immiscible in one another and may be separated from each other following partitioning to the extent that the purity of one phase is not substantially contaminated by the other phase, are suitable, provided that cyclopamine has sufficient solubility to remain in the organic solvent. Preferably, the organic solvent or solvent mixtures will preferentially extract the cyclopamine and not other valuable alkaloids, including for example jervine, veratramine and cyclopasine. In one aspect, the aqueous solvent is water and the organic solvent is ethyl acetate. In a preferred aspect, the organic solvent is a mixture of hexane and ethyl acetate. More preferably, the organic solvent comprises about 30 percent v/v ethyl acetate and 70 percent v/v hexane. A preferred volumetric ratio of aqueous to organic solvents is 1:1 and the preferred number of extraction iterations is three. It will be evident to those skilled in the art that multiple extractions using relatively smaller volumes of organic solvent is more effective than the single use of a larger solvent volume. A practitioner may therefore depart from the volumes of solvents used and number of extractions employed without departing from the scope of the invention.

Following liquid-liquid extraction, the organic phase is separated from the aqueous phase and recovered substantially free of the aqueous phase. It will become evident to those skilled in the art that this separation can be achieved by any known means, including for example centrifugation or decanting. The organic phase is then concentrated to form a second residue enriched in cyclopamine. This second residue can also be named an enriched extract of cyclopamine. The concentration is preferably effected under reduced pressure and at a temperature below which the thermal decomposition of cyclopamine is minimized. Preferably, the concentration is effected at a pressure less than about 25 mm Hg and a temperature less than about 50° C. More preferably, the concentration is effected at a temperature less than 45° C.

In a preferred aspect of the invention, the second residue enriched extract is purified further by precipitating impurities in a suitable organic solvent or organic solvent mixture, separating the precipitated impurities from the remaining cyclopamine-containing organic solution, and concentrating the cyclopamine-containing organic solution to provide a more concentrated enriched extract. Suitable organic solvents include, but are not limited to, methanol, acetonitrile and mixtures thereof. Preferably, the organic solvent is comprised of a mixture of methanol and acetonitrile. More preferably, the organic solvent comprises about 30 percent v/v methanol and 70 percent v/v acetonitrile. In a preferred embodiment, the second residue enriched extract is dissolved in 30 percent v/v methanol/acetonitrile at a temperature of about 70° C., mixed for about 10 to 20 minutes until all solids have been dissolved, and then allowed to settle at a temperature of about 0 to 4° C. for about 8 to 24 hours. Separation of the precipitated impurities can be achieved by any means known in the art, including for example centrifugation or filtration. In a preferred embodiment, the separated impurities are washed with fresh organic solvent mixture prior to being discarded. The remaining cyclopamine-containing organic solution, also known as a filtrate, is then concentrated by any suitable means to form a third residue enriched extract more concentrated in cyclopamine. The concentration is preferably effected under reduced pressure and at a temperature below which the thermal decomposition of cyclopamine is minimized. Preferably, the concentration is effected at a pressure less than about 25 mm Hg and a temperature less than about 50° C. More preferably, the concentration is effected at a temperature less than 45° C.

In another aspect of this invention, the aqueous phase following liquid-liquid extraction is recovered substantially free of the organic phase and subjected to a second liquid-liquid extraction using a second organic solvent or organic solvent mixture capable of extracting the other valuable alkaloids, including for example jervine, veratramine and cyclopasine, from the aqueous phase. The organic phase containing the other valuable alkaloids can then be recovered from the organic phase and concentrated to form a fourth residue. The fourth residue can then be subjected to a further finishing treatment to recover the other steroidal alkaloids, such finishing treatment including but not limited to crystallization, chromatography or mixtures thereof.

In another embodiment of this invention, an improvement is made to the process wherein the extractant is an aqueous alcohol (e.g., alcohol-water mixture) that is made basic or alkaline by the addition of a suitable base including, but not limited to, ammonia. The alcohol can be any lower alcohol including ethanol, methanol or isopropyl alcohol or mixtures thereof. Preferably, the alcohol is ethanol. It is believed that the addition of a suitable base improves the extraction efficiency and prevents possible decomposition of the basic alkaloid cyclopamine. The aqueous alcohol extractant can be composed of about 50 to 95 v/v percent alcohol. Preferably, the aqueous alcohol extractant comprises about 60 to 70 v/v percent alcohol. In one embodiment, the aqueous component of the extractant includes about 5 percent w/w ammonia. In a preferred embodiment, the extractant is made basic by the addition of a suitable base including, but not limited to, sodium carbonate to the cyclopamine-containing organic matter prior to contact with the extractant. About 0.05 to 0.20 kg of sodium carbonate is added per kg of organic matter. Preferably, about 0.09 to 0.12 kg of sodium carbonate is added per kg of organic matter.

In a preferred embodiment of this invention, extraction of the organic matter is promoted by microwave-assisted extraction. Cyclopamine containing organic matter, in any physical form, is mixed with a solvent which is relatively transparent to microwaves, compared with the organic matter, and exposed to microwave radiation until access to cyclopamine by the solvent is facilitated. While not wishing to be bound by theory, the application of microwave energy to the system causes microwave energy to be preferentially absorbed by the material being treated, compared to the extractant, leading to a positive differential in temperature between the organic material and the extractant, ensuring that the substance to be extracted migrates towards the extractant. Further, it is believed that the application of microwave energy to the system results in in-core heating of the organic matter resulting in a rapid buildup of pressure within cells which can disrupt the microstructure and facilitate access of the solvent to the substance to be extracted. The use of microwave-assisted extraction can result in reduced extraction times, reduced extractant-to-organic matter ratio requirements, increased recovery of cyclopamine and improved purity of the second residue enriched extract.

The invention also provides a process for separating cyclopamine from the enriched extract comprising the steps of:
(a) Providing an enriched extract containing cyclopamine in a solvent suitable for loading onto a normal phase chromatography column;
(b) Loading the cyclopamine comprising mixture onto a normal phase chromatography column packed with a solid support in a solvent suitable as a mobile phase; and
(c) Separating the cyclopamine by eluting the normal phase chromatography column with a mobile phase having a sufficient polarity to elute cyclopamine.

To prepare the enriched extract for running on a chromatography column, a suitable solid support such as diatomaceous earth or Celite can be combined with the concentrated cyclopamine-containing organic phase and evaporating to dryness, thereby adhering the cyclopamine to the solid support. In another embodiment, the enriched extract can be triturated (digested) either once or repeatedly with an organic solvent which dissolves the cyclopamine. The preferred organic solvent is toluene. The enriched extract dissolved in the organic solvent is combined with a solid support and evaporated to dryness. More preferably, the enriched extract dissolved in the organic solvent is combined with silica gel and evaporated to dryness under vacuum.

The cyclopamine-containing solid support is then loaded directly onto a packed normal phase chromatography column and a mobile phase capable of separating the cyclopamine from the other components is passed through the chromatography column. The preferred normal phase column chromatography packing material stationary phase is silica gel. More preferably, the packing material is silica gel 230 to 400 mesh. The mobile phase comprises (1) a non-polar component selected from a group consisting of hexane, petroleum ether, toluene, benzene and solvents having similar polarities, and (2) a polar component selected from acetone, ethyl acetate, ether, chloroform, acetonitrile and solvents having similar polarities. Preferably, the mobile phase comprises toluene and acetone. In a preferred embodiment, a small amount of triethylamine is also included in the mobile phase mixture. In a more preferred embodiment, the volumetric ratio of acetone:toluene:TEA is about 50:50:0.5. Alternatively, any series of solvent mixtures having polarities similar to those of the acetone/toluene mixtures described above are suitable.

Preferably, the normal phase chromatography column is run under pressure. The dimensions of the column are selected according to the quantity of cyclopamine to be separated. Any suitable column loading of enriched extract to packing material and mobile phase flow rate may be used that provides reasonable resolution of cyclopamine separation. For a 15 by 130 cm column containing about 10 kg of silica gel, the typical pressure is about 25 psig, the typical loading is about 0.1 to 0.2 kg of enriched extract per kg of packing material, and the typical mobile phase flow rate is about 10 to 15 L/h.

The mobile phase is collected in fractions until at least one fraction is collected that contains cyclopamine. The presence of cyclopamine in the fractions may be detected by thin layer chromatography (TLC) when run against a cyclopamine standard using for example normal phase alumina silica plates, and ethyl acetate/dichloromethane/methanol as the developing system and potassium permanganate as the visualizing reagent. The presence of cyclopamine in the fractions may also be detected by any other means typical in the art, including for example HPLC (high performance liquid chromatography), without departing from the scope of the invention. When more than one fraction containing cyclopamine is collected, at least some of the fractions containing cyclopamine can be combined. The single or combined fractions are then concentrated to obtain a cyclopamine-rich residue. In a preferred embodiment, the concentration is effected under reduced pressure and at a temperature below which the thermal decomposition of cyclopamine is minimized. Preferably, the concentration is effected at a pressure less than about 25 mm Hg and a temperature less than about 50° C. More preferably, the concentration is effected at a temperature less than 45° C.

Following chromatography, the cyclopamine-rich residue obtained from the at least one fraction containing cyclopamine can be crystallized using a crystallizing solvent to obtain purified cyclopamine crystals. Suitable crystallizing solvents include, but are not limited to, acetone, methanol, acetonitrile, hexane, and mixtures thereof. Preferably, the crystallizing solvent is comprised of a mixture of hexane and acetone. More preferably, the organic solvent comprises about 30 percent v/v acetone and 70 percent v/v hexane, including for example, between 50 percent v/v hexane and 70 percent v/v hexane to acetone. In a preferred embodiment, the cyclopamine-rich residue is dissolved in the acetone/hexane mixture at a ratio of about 1 kg of residue per 2 L of crystallizing solvent and at a temperature of about 50 to 60° C., and the cyclopamine crystals allowed to crystallize over a period of about 6 to 24 hours at a temperature of about 2 to 8° C. Following crystallization, the cyclopamine crystals are separated from the crystallizing solvent mixture, washed with fresh crystallizing solvent and dried. In a preferred embodiment, the crystallizing solvent is comprised of 50% hexane/50% acetone (v/v) and the wash mixture is comprised of 70% hexane/30% acetone (v/v).

In one aspect of this invention, the purified cyclopamine crystals are recrystallized one or more times to increase their purity. Suitable recrystallizing solvents include, but are not limited to, acetone, methanol, acetonitrile, hexane, and mixtures thereof. Preferably, the recrystallization solvent is comprised of a mixture of methanol and acetonitrile. More preferably, the recrystallization solvent comprises about 65 percent v/v methanol and about 35 percent v/v acetonitrile. In a preferred embodiment, the purified cyclopamine crystals are dissolved in the methanol/acetonitrile mixture at a ratio of about 1 kg of cyclopamine crystals to 3 L of recrystallizing solvent and at a temperature of about 50 to 60° C., and the cyclopamine crystals allowed to crystallize over a period of about 6 to 24 hours at a temperature of about 2 to 8° C. Following recrystallization, the cyclopamine crystals are separated from the recrystallizing solvent mixture, washed with fresh recrystallizing solvent and dried.

EXAMPLES

Example 1

Approximately 25 g of dried, finely ground roots of *V. californicum* were contacted with 250 mL of different extractant solvent mixtures and slowly agitated at ambient temperature for 4 hours. The extracted solids were then separated from the extract solution by filtration. The extracted solids were washed with a further 50 mL of fresh solvent and the combined extract/wash solution concentrated under vacuum using a rotary evaporator operating at approximated 45° C. to form a dried residue. Samples of the residues were quantitatively analysed for cyclopamine content by RPHPLC against a cyclopamine standard. Table 1 shows the total extract yield obtained (g residue per g of starting dried roots) and the purity of the extract residues obtained (weight % cyclopamine).

TABLE 1

Extraction of dried, ground *v. californicum* roots in different solvents

| Solvent Mixture | Total Extract Yield (%) | Cyclopamine concentration in Extract (% w/w) |
|---|---|---|
| hexane + 5% sodium carbonate | 0.3% | 2.7% |
| ethanol | 6.9% | 1.8% |
| ethanol/water (67:33 v/v) + 5% sodium carbonate | 4.5% | 2.7% |

Example 2

Approximately 25 g of dried, finely ground roots of *V. californicum* were contacted with 250 mL of different extractant solvent mixtures and extracted by microwave-assisted extraction. The root/solvent mixtures were gently agitated in a modified laboratory-scale microwave extractor connected to a condenser system and subjected to 300 Watts microwave energy at 2450 Mhz for 5 minutes. The mixture was then gently agitated for 25 minutes following microwave exposure. The extracted solids were then separated from the extract solution by filtration. The extracted solids were washed with a further 50 mL of fresh solvent and the combined extract/wash solution concentrated under vacuum using a rotary evaporator operating at 45° C. to form a dried residue. Samples of the residues were quantitatively analysed for cyclopamine content by RPHPLC against a cyclopamine standard. Table 2 shows the total extract yield obtained (g residue per g of starting dried roots) and the purity of the extract residues obtained (weight % cyclopamine).

TABLE 2

Microwave-assisted extraction of dried, ground *v. californicum* roots in different solvents

| Solvent Mixture | Total Extract Yield (%) | Cyclopamine concentration in Extract (% w/w) |
|---|---|---|
| hexane + 5% sodium carbonate | 0.6% | 7.8% |
| ethyl acetate | 1.9% | 3.3% |
| dichloromethane | 1.7% | 4.2% |
| ethyl acetate/methanol (90:10 v/v) | 3.8% | 2.8% |
| dichloromethane/methanol (80:20 v/v) | 6.7% | 2.9% |
| ethanol | 13.4% | 2.7% |
| ethanol/water (67:33 v/v) + 5% sodium carbonate | 4.2% | 7.8% |

Example 3

Approximately 25 g of dried, finely ground *V. californicum* roots containing 2.4 g/kg of cyclopamine was mixed with 4.15 g of sodium carbonate and contacted with 250 mL of 67% ethanol/33% water (v/v). The mixture was placed in a modified laboratory-scale microwave extractor connected to a condenser system and subjected to 300 Watts microwave energy at 2450 Mhz for 5 minutes under gentle agitation. The mixture was agitated for a further 25 minutes following microwave exposure. The extracted solids were then separated from the extract solution by filtration. The extract solution was concentrated under vacuum using a rotary evaporator operating at 45° C. to a volume of approximately 25 mL to form a concentrated first residue aqueous solution. The first residue was combined with 25 mL of 70% hexane/30% ethyl acetate (v/v) organic solution, mixed for 15 minutes and then transferred to a separatory funnel for 1 hour. The organic phase was collected and the aqueous phase re-contacted two more times with organic solution. The organic phases were separated from the aqueous phase, combined and concentrated to dryness under vacuum in a rotary evaporator, producing 0.47 g of a second residue containing approximately 10.5% cyclopamine (w/w). The aqueous phase was extracted three times with equal volumes of ethyl acetate, the organic phase separated from the aqueous phase, and the ethyl acetate layers combined and concentrated to dryness under vacuum in a rotary evaporator to produce 0.29 g of a third residue. The third residue contained less than 1% of cyclopamine (w/w) and displayed HPLC peaks consistent with jervine, veratramine and cycloposine.

Example 4

Approximately 50 g of dried, finely ground *V. californicum* roots containing 2.4 g/kg of cyclopamine was mixed with 8.3 g of sodium carbonate and contacted with 500 mL of 67% ethanol/33% water (v/v). The mixture was placed in a modified laboratory-scale microwave extractor connected to a condenser system and subjected to 300 Watts microwave energy at 2450 Mhz for 5 minutes under gentle agitation. The mixture was agitated for a further 25 minutes following microwave exposure. The extracted solids were then separated from the extract solution by filtration. The extract solution was concentrated under vacuum using a rotary evaporator to a volume of approximately 50 mL to form a concentrated first residue aqueous solution. The first residue was combined with 50 mL of hexane, mixed for 15 minutes and then transferred to a separatory funnel for 1 hour. The organic phase was collected and the aqueous phase re-contacted two more times with hexane. The organic phases were separated from the aqueous phase, combined and concentrated to dryness under vacuum in a rotary evaporator, producing 0.26 g of a second residue containing approximately 20.6% cyclopamine (w/w). The aqueous phase was extracted three times with equal volumes of dichloromethane, and the dichloromethane layers separated from the aqueous phase, combined and concentrated to dryness under vacuum in a rotary evaporator to produce 0.52 g of a third residue containing approximately 8.7% cyclopamine (w/w). The remaining aqueous phase was extracted three times with equal volumes of ethyl acetate, and the ethyl acetate layers separated from the aqueous phase, combined and concentrated to dryness under vacuum in a rotary evaporator to produce 0.57 g of a third residue containing approximately 3.8% cyclopamine (w/w).

Example 5

Approximately 10 kg of dried, milled *V. californicum* roots was mixed with 1.1 kg of sodium carbonate and fed at a constant rate of 4 kg/h through a continuous, auger-driven microwave-assisted extractor. 100 L of 67% ethanol/33% water (v/v) extractant was fed concurrently with the biomass at a rate of 40 L/h. The residence time in the microwave cavity was approximately 2 minutes at 1700 Watts, 2450 Mhz and the post-microwave mixing time was 30 minutes. Following extraction, the extracted biomass was separated from the extract solution by filtration. The extract solution was collected and concentrated under vacuum to a final volume of approximately 30 L. The concentrated first residue aqueous solution was then combined with an equal volume of 70% hexane/30% ethyl acetate (v/v) organic solution, mixed for 15 minutes and allowed to settle for 90 minutes. The organic phase was separated from the aqueous phase by decanting and the aqueous phase re-contacted two more times with an equal volume of 70% hexane/30% ethyl acetate organic solution. The solutions were again mixed for 30 minutes, allowed to settle for 90 minutes and the organic phase separated from the aqueous phase by decanting. The organic phases were then combined and the mixture concentrated under vacuum to form a second residue concentrated in cyclopamine. The second residue was approximately 172 g of dried, enriched extract containing about 13% cyclopamine (w/w).

Example 6

One gram samples of the enriched extract obtained in Example 5 were loaded onto a 2.3 cm internal diameter by 34 cm long glass column packed with 10 g of 230-400 mesh silica gel. The columns were eluted by gravity flow using different organic solvent mixtures as the mobile phase. Eluant fractions of 20 mL were collected and the presence of cyclopamine in the fractions detected by thin layer chromatography (TLC) run against a cyclopamine standard. Fractions containing cyclopamine were combined and evaporated to dryness under vacuum using a rotary evaporator. The dried, combined fractions were analysed for cyclopamine content by RPHPLC against a cyclopamine standard. Table 3 shows the results of the column chromatography experiments using the different mobile phase mixtures.

TABLE 3

Effect of mobile phase composition on column chromatography separation of cyclopamine.

| Mobile Phase Composition | Cyclopamine concentration in combined fractions (% w/w) | % Recovery of available cyclopamine through column (%) |
|---|---|---|
| ethyl acetate:DCM:methanol:TEA (80:10:10:0.5) | 45% | 52% |
| ethyl acetate:DCM:methanol:TEA (85:10:5:0.5) | 55% | 56% |
| ethyl acetate:DCM:methanol:TEA (82:10:8:0.05) | 45% | 54% |
| acetone:toluene:TEA (50:50:0.5) | 92% | 96% |

Example 7

164 kg of dried, milled *V. californicum* roots containing approximately 4 g/kg of cyclopamine was mixed with 24 kg of sodium carbonate and charged to a 600 gallon stainless steel reactor containing 1200 L of 67% ethanol/33% water (v/v) extractant. The mixture was agitated for 14 hours at 60° C. The extracted biomass was separated from the extract solution by filtration and the filter cake washed with an additional 300 L of fresh extractant and the wash solution combined with the extract solution. A total of approximately 1500 L of filtrate extract solution was collected and concentrated to approximately 500 L at 25 mm Hg and 40° C. using a 200 gallon reactor to form a first residue. The concentrated first residue aqueous solution was then combined with an equal volume of 70% hexane/30% ethyl acetate (v/v) organic solution in a 200 gallon reactor, mixed for 15 minutes and allowed to settle for 60 minutes. The organic phase was separated from the aqueous phase by decanting and the aqueous phase re-contacted two more times with an equal volume of 70% hexane/30% ethyl acetate organic solution. The solutions were again mixed for 15 minutes, allowed to settle for 60 minutes and the organic phase separated from the aqueous phase by decanting. The organic phases were then combined, 10 mL of triethylamine added and concentrated under vacuum to form a second residue concentrated in cyclopamine. The second residue was approximately 35 L of concentrated organic phase containing 5.6 kg of cyclopamine-enriched solids. The solids were analysed for cyclopamine content by RPHPLC against a cyclopamine standard and found to contain about 7.5% cyclopamine (w/w).

Example 8

Approximately 2 kg of the second residue enriched extract solids from Example 7 were dissolved in 4 L of methanol using a 20 L rotary evaporator. The dissolution temperature was 70° C. and the dissolution time was 20 minutes. The temperature of the mixture was lowered to 50° C. and 10 L of acetonitrile was slowly added. The mixture was then placed in a cold room and maintained at between 0 and 4° C. for approximately 12 h. The mixture was then filtered under vacuum to remove the precipitated impurities from the remaining cyclopamine-containing methanol/acetonitrile organic solution. The organic solution was then concentrated to dryness leaving 920 g of concentrated residue containing about 16% cyclopamine (w/w).

Example 9

108 kg of dried, milled *V. californicum* roots containing approximately 2.1 g/kg cyclopamine was mixed with 10 kg of sodium carbonate and fed at a constant rate of 12 kg/h through a continuous, auger-driven microwave-assisted extractor. 480 L of 67% ethanol/33% water (v/v) extractant was fed concurrently with the biomass at a rate of approximately 53 L/h. The residence time in the microwave cavity was approximately 2 minutes at 1700 Watts, 2450 Mhz and the post-microwave mixing time was 30 minutes. Following extraction, the extracted biomass was separated from the extract solution by filtration. A total of 365 L of extract solution was collected and concentrated to a final volume of 96 L at 25 mm. Hg and 40° C. using a 400 L reactor to form a first residue. The concentrated first residue aqueous solution was then combined with an equal volume of 70% hexane/30% ethyl acetate (v/v) organic solution, mixed for 15 minutes and allowed to settle for 45 to 60 minutes. The organic phase was separated from the aqueous phase by decanting and the aqueous phase re-contacted two more times with an equal volume of 70% hexane/30% ethyl acetate organic solution. The solutions were again mixed for 15 minutes, allowed to settle for 45 to 60 minutes and the organic phase separated from the aqueous phase by decanting. The organic phases were then combined, 10 mL of triethylamine added and the mixture concentrated under vacuum to form a second residue concentrated in cyclopamine. The second residue was approximately 2.1 kg of dried, enriched extract. The second residue was analysed for cyclopamine content by RPHPLC against a cyclopamine standard and found to contain about 10% cyclopamine (w/w).

1.6 kg of the second residue enriched extract was dissolved in toluene, combined with 2.25 kg of 70-230 mesh silica gel and evaporated to dryness using a 20 L rotary evaporator operating at approximately 25 mm Hg and 45° C. A 15 cm internal diameter, 130 cm long glass column was packed with approximately 8 kg of 230-400 mesh silica gel and equilibrated with a mobile phase comprised of a mixture of acetone: toluene:triethylamine at a volumetric ratio of approximately 50:50:0.5. The enriched extract/silica gel mixture was then loaded onto the top of the column and the column was eluted by pumping the mobile phase through the column at a pressure of approximately 25 psig and a flowrate of 12 L/h. Eluant fractions of between 1 and 2 L were collected and the presence of cyclopamine in the fractions detected and monitored by thin layer chromatography (TLC) run against a cyclopamine standard using normal phase alumina silica plates, and ethyl acetate/dichloromethane/methanol as the developing system and potassium permanganate as the visualizing reagent. Approximately 60 cyclopamine-containing fractions were segregated and combined into five groups and evaporated to dryness under vacuum using a 20 L rotary evaporator. The dried, combined fractions were quantitatively analysed for cyclopamine content by RPHPLC against a cyclopamine standard. Table 4 shows the mass of fractions collected and the purity of the dried fractions obtained (weight % cyclopamine).

TABLE 4

Cyclopamine fractions collected from column chromatography

| Fraction | Mass dried residue (g) | Cyclopamine Purity (% w/w) |
| --- | --- | --- |
| A ½ | 72.5 | 49% |
| A ²/² | 64.4 | 56% |
| A1 | 44.8 | 54% |
| A2 | 46.6 | 46% |
| B2 | 29.6 | 40% |

64.4 g of fraction A 2/2 containing approximately 56% cyclopamine (w/w) was dissolved in 120 mL of 50% hexane/50% acetone (v/v) at 55° C. The solution was then placed in a refrigerator at approximately 4° C. for approximately 12 hours to crystallize cyclopamine. The crystals were separated from the crystallization solvent by vacuum filtration, washed with 65 mL of a cold solution of 70% hexane/30% acetone (v/v), and dried under vacuum resulting in 21.2 g of purified cyclopamine containing >97% cyclopamine.

The invention claimed is:

1. A process for extracting, purifying and isolating cyclopamine from cyclopamine-containing biomass comprising the steps of:
    Mixing the cyclopamine-containing organic matter with an aqueous solvent, which solvent is transparent to microwaves;
    extracting cyclopamine using microwave-assisted technology to obtain a cyclopamine/extract solution separating the extracted organic matter from the cyclopamine/extract solution;
    concentrating the cyclopamine/extract solution leaving a concentrated aqueous solution;
    contacting the concentrated aqueous solution with an organic extractant capable of selectively extracting cyclopamine from the aqueous phase;
    concentrating the cyclopamine-containing organic phase, providing an enriched extract containing cyclopamine;
    separating cyclopamine from the enriched extract using column chromatography, providing at least one fraction containing cyclopamine; and
    crystallizing select chromatography fractions to provide purified cyclopamine.

2. A process for obtaining cyclopamine from cyclopamine-containing biomass, the improvement comprising the preparation of a second residue following the initial extraction of cyclopamine-containing organic matter which is more highly concentrated in cyclopamine, said improvement comprising the steps of:
    extracting the cyclopamine-containing organic matter into an aqueous solvent capable of extracting cyclopamine using microwave-assisted technology to obtain a cyclopamine/extract solution;
    separating the extracted organic matter from the cyclopamine/extract solution;
    concentrating the cyclopamine/extract solution to form a first residue;
    partitioning the residue between an aqueous phase and an organic solvent or solvent mixture capable of dissolving the cyclopamine to produce an aqueous phase and an organic phase;
    separating the organic phase from the aqueous phase and recovering the organic phase substantially free of the aqueous phase;
    forming a second residue from the organic phase enriched in cyclopamine.

3. The process according to claim 2, wherein the second residue is optionally subjected to a finishing treatment to further purify or isolate cyclopamine.

4. The process according to claim 3, wherein the finishing treatment comprises at least one of liquid-liquid extraction, precipitation, crystallization, or chromatography treatment.

5. The process according to claim 4, wherein the finishing treatment comprises dissolving the second residue in an organic solvent or solvent mixture, precipitating impurities from the solvent or solvent mixture, separating the precipitated impurities from the remaining cyclopamine-containing organic solution, and concentrating the cyclopamine-containing organic solution to provide a more concentrated residue.

6. The process according to claim 5, wherein the organic solvent is methanol, acetonitrile, or a mixture of ethanol and acetonitrile.

7. The process according to claim 2, wherein the aqueous phase from the separation step is recovered substantially free of the organic phase and subjected to a further finishing treatment to recover steroidal alkaloids.

8. The process according to claim 7, wherein the steroidal alkaloids recovered are jervine, veratramine and cyclopasine.

9. The process according to claim 1, wherein the biomass contains *Veratrum Californicum* biomass.

10. The process according to claim 1, wherein the biomass is subjected to an initial drying step.

11. The process according to claim 10, wherein the biomass is dried to a residual moisture content of less than 20% by weight.

12. The process according to claim 1, wherein the extractant is an ethanol-water mixture.

13. The process according to claim 12 wherein the extractant is an ethanol-water mixture composed of between 50 and 95 percent v/v ethanol.

14. The process according to claim 12 wherein the extractant is and ethanol-water mixture composed of between 60 and 70 percent v/v ethanol.

15. The process according to claim 1, wherein the cyclopamine-containing organic matter is mixed with a suitable base before contacting with an extractant capable of extracting cyclopamine.

16. The process according to claim 15, wherein the base is sodium carbonate.

17. The process according to claim 15, wherein cyclopamine-containing organic matter is mixed with between the 0.05 and 0.20 kilograms of sodium carbonate before contacting with an extractant capable of extracting cyclopamine.

18. The process according to claim 2, wherein the organic solvent is ethyl acetate.

19. The process according to claim 2, wherein the organic solvent mixture is a mixture of hexane and ethyl acetate.

20. The process according to claim 2, wherein the organic solvent is a mixture comprised of approximately 70% hexane/30% ethyl acetate by volume.

* * * * *